United States Patent [19]

Latov et al.

[11] Patent Number: 5,429,929
[45] Date of Patent: Jul. 4, 1995

[54] METHOD FOR DETECTING ANTIBODIES TO A NEUROBLASTOMA ANTIGEN IN MENTAL ILLNESS

[75] Inventors: Norman Latov, Hartsdale, N.Y.; Saud A. Sadiq, Teaneck, N.J.; Jack M. Gorman, Riverdale; Costas Kilidireas, New York, both of N.Y.

[73] Assignee: The Trustees of Columbia University in the City of New York, New York, N.Y.

[21] Appl. No.: 688,748

[22] Filed: Apr. 19, 1991

[51] Int. Cl.$^6$ ............... G01N 33/543; G01N 33/564
[52] U.S. Cl. ............................ 435/7.9; 435/7.23; 435/7.92; 435/7.93; 435/7.95; 436/506; 436/518; 436/531; 436/536; 436/539; 436/540; 436/811
[58] Field of Search ............ 435/7.23, 7.9, 7.92, 435/7.93, 7.95; 436/506, 513, 539, 518, 531, 536, 540, 800, 804, 811; 530/326, 839

[56] References Cited

U.S. PATENT DOCUMENTS

| | | | |
|---|---|---|---|
| Re. 29,474 | 11/1977 | Axen et al. | 436/529 |
| 3,551,555 | 12/1970 | Schuurs | 436/534 |
| 3,553,310 | 1/1971 | Csizmas et al. | 424/2 |
| 3,646,346 | 2/1972 | Catt | 436/531 |
| 3,720,760 | 3/1973 | Bennich et al. | 436/513 |
| 4,048,298 | 9/1977 | Niswender | 436/500 |
| 4,092,408 | 5/1978 | Litt | 436/531 |
| 4,210,418 | 7/1980 | Brown et al. | 436/532 |
| 4,528,267 | 7/1985 | Calenoff et al. | 435/7.92 |
| 4,666,829 | 5/1987 | Glenner et al. | 435/6 |
| 4,728,605 | 3/1988 | Fudenberg et al. | 435/29 |
| 4,874,694 | 10/1989 | Gandy et al. | 435/15 |

FOREIGN PATENT DOCUMENTS

WO8912455 12/1989 WIPO.

OTHER PUBLICATIONS

Wisdom et al. "Enzyme–Immunoassay" Clinical Chemistry, vol. 22, No. 8 1976 pp. 1243–1255.
Sudin et al. "Antibody Reactivity to Brain Membrane Proteins in Serum from Schizophrenic Patients" Brain, Behav. Immunology, vol. 3 (4), pp. 345–348 (Abstract) 1989.
Maggio, Enzyme–Immunoassay, CRC Press, Inc., Boca Raton, Fla., 27–33, 45–52 (1987).
Mogilina, N. P., et al., Zh Nevropatol Psikhiatr, (1981), vol. 81, No. 3, pp. 397–401, (Russian language) (Abstact, English language), (Exhibit 4).
Sundin U., et al., Brain, Behavior, Immunity, (1989), vol. 3, No. 4, pp. 345–358, (Abstract), (Exhibit 5).
Sundin, U., et al. Brain, Behavior, Immunity, (1989), vol. 3, No. 4, pp. 345–358, (Exhibit 7).
DeLisi, L. E., et al., Biological Psychiatry, (1985), vol. 20, No. 1, pp. 110–115.
Ganguli, R., et al., Annals Of The New York Academy of Sciences, (1987), vol. 496, pp. 676–685, (Exhibit 9).

(List continued on next page.)

Primary Examiner—David Saunders
Attorney, Agent, or Firm—John P. White

[57] ABSTRACT

The subject invention provides an antigen characterized as having a molecular weight of approximately 68 kD, being reactive with autoantibodies associated with mental illness especially schizophrenia, being located in neuronal cells, and co-migrating with a protein band in SDS-PAGE which is recognized by rabbit antibodies which react with the peptide whose sequence is Ala-Lys-Xaa-Val-Lys-Phe-Gly-Ala-Asp-Ala-Xaa-Ala-Leu-Met-Leu (SEQ ID NO: 2). The invention also provides methods for detecting in a sample from a subject the presence of an antibody to the neuronal antigen, determining the propensity of a subject toward a psychiatric disease, diagnosing and treating a subject having mental illness.

36 Claims, 3 Drawing Sheets

OTHER PUBLICATIONS

Cuatrecasas, P., *Journal of Biological Chemistry*, (1970), vol. 245, No. 12, pp. 3059–3065, (Exhibit 10).

Mena, M. A., et al., *Brain Research*, (1989), vol. 486, No. 2, pp. 286–296, (Exhibit 11).

Norton, W. T., in Fleischer, S., et al., *Methods In Enzymology*, (1974), vol. 31, Part A, Academic Press, New York, pp. 435–444, (Exhibit 12).

Hoffman, E. P., et al., *Cell*, (1987), vol. 51, pp. 919–928, (Exhibit 13).

Lowry, O. H., et al., *Journal Of Biological Chemistry*, (1951), vol. 193, pp. 265–275, (Exhibit 14).

Laemmli, U. K., *Nature*, (1970), vol. 227, pp. 680–685, (Exhibit 15).

Towbin, H., et al., *Proceedings Of The National Academy of Sciences USA*, (1979), vol. 76, No. 9, pp. 4350–4354, (Exhibit 16).

Matsudaira, P., *Journal Of Biological Chemistry*, (1987), vol. 262, No. 21, pp. 10035–10038, (Exhibit 17).

Van den Berg, L. H., et al., *Journal Of Neuroscience Research*, (1990), vol. 25, No. 3, pp. 295–299, (Exhibit 18).

Jindal, S., et al., *Molecular And Cellular Biology*, (1989), vol. 9, No. 5, pp. 2279–2283, (Exhibit 32).

Flood, J. F., et al., *Proceedings Of The National Academy Of Sciences, USA*, (1991), vol. 88, pp. 3363–3366, (Exhibit 33).

METHOD FOR DETECTING ANTIBODIES TO A NEUROBLASTOMA ANTIGEN IN MENTAL ILLNESS

BACKGROUND OF THE INVENTION

Throughout this application, various publications are referenced within parentheses. The disclosures of these publications in their entireties are hereby incorporated by reference into this application in order to more fully describe the state of the art as known to those skilled therein as of the date of the invention described and claimed herein.

It has been suggested that autoantibodies may cause schizophrenia or mental illness, and that patients with schizophrenia or mental illness may have antibodies to specific antigens in human neurons, but to date, such antigens have not been identified or well characterized (DeLisi, L. E., Weber, R. J., Pert, C. B., Are there antibodies against brain in sera from schizophrenic patients? Review and Prospectors. Biol. Psychiatry 1985; 20: 94–119; Ganguli, R., Rabin, B. S., Kelly, R. H., Lyte, M., Ragu, U., Clinical and laboratory evidence of autoimmunity in acute schizophrenia. Annals New York Academy of Science 1987; 496: 676–685).

The subject invention describes antibodies from patients with schizophrenia that react with an antigen expressed in human neuroblastoma cells in tissue culture and in the human central nervous system.

SUMMARY OF THE INVENTION

The subject invention provides an antigen characterized as having a molecular weight of approximately 68 kD, being reactive with antibodies associated with mental illness, being located in neuronal cells, and having the same mobility on SDS-PAGE as a protein recognized by rabbit antibodies to the sequence alanine-lysine-alanine-valine-lysine-phenylalanine-glycine-alanine-aspartic acid-alanine-lysine-alanine-leucine-methionine-leucine, SEQ. ID NO: 1.

The invention also provides a method for detecting in a sample from a subject the presence of an antibody to the neuroblastoma antigen. Any assay may be used to detect the neuronal antigen, such as radioimmunoassays, immunoblot, such as Western blot, assays, and immunoprecipitation assays.

The invention additionally provides a diagnostic method for determining the propensity of a subject toward mental illness and a diagnostic method for monitoring the progression or regression of mental illness in a subject. The invention further provides a method for treating a subject having mental illness.

BRIEF DESCRIPTION OF THE FIGURES

FIG. 2 shows western blot analysis of protein extracts of neuroblastoma cells (lane C) and of human spinal cord non-myelin (lane B) and myelin (lane A) membrane fractions. Blots are immunostained with IgG from a patient with schizophrenia. The immunoreactive 68 kD protein band (arrow) is present in the neuroblastoma preparation and in the spinal cord non-myelin membrane fraction.

DETAILED DESCRIPTION OF THE INVENTION

Figure 1:
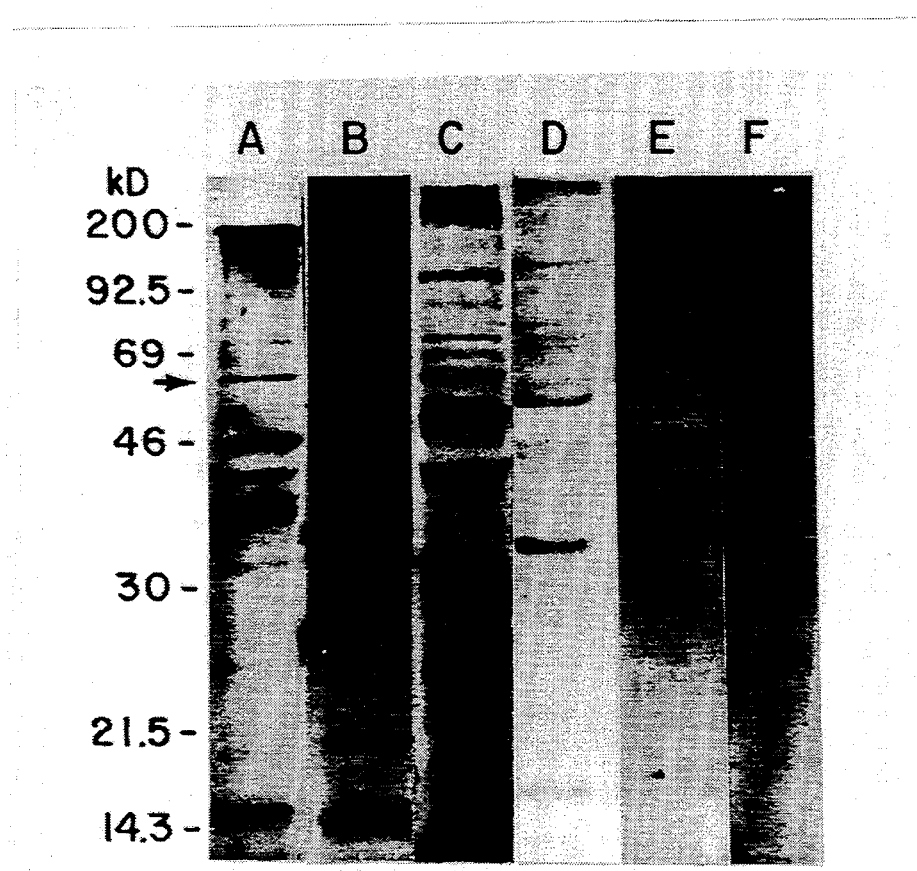
FIG. 1. Western blot analysis of neuroblastoma proteins immunostained with serum IgG from patients with schizophrenia and controls. Neuroblastoma proteins were separated by SDS-PAGE, transferred to nitrocellulose sheets and immunostained with serum IgG from patients with schizophrenia (lanes A to C) or controls (lanes D to F). Patients with schizophrenia, but not controls, have IgG antibodies that bind to a protein with approximate mobility of 68 kD (arrow).

The subject invention provides a purified antigen characterized as having a molecular weight of approximately 68 kD, being reactive with antibodies associated with mental illness, being located in neuronal cells, and having an $NH_2$-terminus amino acid sequence as follows: alanine-lysine-Xaa-valine-lysine-phenylalanine-glycine-alanine-aspartic acid-alanine-Xaa-alanine-leucine-methionine-leucine, SEQ ID NO: 2.

In the above amino acid sequence, X is most likely alanine. The antigen has the same mobility on SDS-PAGE as a protein which is reactive with a rabbit antibody to a peptide having the sequence alanine-lysine-alanine-valine-lysine-phenylalanine-glycine-alanine-aspartic acid-alanine-lysine-alanine-leucine-methionine-leucine, SEQ ID NO: 1.

The invention further provides the neuronal antigen labeled with a detectable marker such as an enzyme, a paramagnetic ion, biotin, a fluorophore, a chromophore, a heavy metal, or a radioisotope.

The invention also provides a method for detecting in a sample from a subject the presence of an antibody to the neuronal antigen. Any assay may be used to detect the neuronal antigen, such as radioimmunoassays, immunoblot, such as Western blot, assays, and immunoprecipitation assays.

The method comprises treating the sample with the antigen under conditions permitting binding of the antibody to the antigen and detecting the presence of the antibody bound to the antigen and thereby detecting the presence of the antibody in the sample. This method may also be performed using the labeled antigen. In this method, the detection of the presence of the antibody bound to the reagent may be effected spectrophotometrically. In the preferred embodiments of the method, the antibody being detected is associated with a schizophrenia or mental illness. The sample may be any suitable biological fluid such as blood, plasma, or serum.

The method may be performed where the antibody is immobilized on a solid support such as an ELISA plate. In such an embodiment, the solid support to which the labeled antigen is bound is contacted with the sample under conditions such that any antibody present in the sample binds to the bound antigen and forms a complex therewith, and any antibody which is not bound to the complex is removed. The presence of antibody in the sample can then be qualitatively or quantitatively determined.

Examples of procedures for binding of antibodies to insoluble supports are described in U.S. Pat. Nos. 3,551,555, 3,553,310, 4,048,298 and RE-29,474. Binding of antibodies to polystyrene by adsorption has been described in U.S. Pat. Nos. 3,646,346 and 4,092,408, for example. Binding of protein containing antigens to a variety of insoluble supports has been described in U.S. Pat. No. 3,720,760. Additionally antibodies can be bound to a solid support by adsorption, ionic bonding, van der Waals adsorption, electrostatic bonding, or other non-covalent bonding, or it can be bound to a support by covalent bonding. Procedures for non-covalent bonding are described in U.S. Pat. No. 4,528,267. Procedures for covalently bonding antibodies and antigens to insoluble supports are described by Ichiro Chibata [Immobilized Enzymes, Halsted Press: New York (1978)] and A. Cuatrecasa, [J. Bio. Chem., 245:3059 (1970)]. The surface can be coated with a protein and coupled with the antibody or antigen using procedures described in U.S. Pat. No. 4,210,418 using glutaraldehyde as a coupling agent, for example. In a still further procedure, the antibody or antigen can be coupled to a hydroxylated material by means of cyanogen bromide as described in U.S. Pat. No. 3,720,760. The proceding are examples of ways to immoblize an antibody on a solid suport, they are in no way intended to limit the claimed invention.

In another embodiment, the solid support to which the antigen is bound is contacted with the sample under conditions such that any antibody present in the sample binds to the bound antigen and forms a complex therewith, removing any antibody which is not bound to the complex, contacting any complex so formed with a labeled antihuman antibody which specifically binds to any antibody present in the complex so as to form a second complex which includes the antigen, antibody, and labeled antihuman antibody. In one embodiment of this method, the antihuman antibody is labeled with a detectable marker, such as a radioisotope, fluorescent dye, or enzyme. The presence of antibody in the sample can be qualitatively determined, or the amount of antibody in the sample can be quantitatively determined. The antihuman antibody may be labeled with an enzyme and the second complex contacted with a substrate specific to the enzyme under conditions such that the enzyme reacts with the substrate to form a detectable product. The enzyme may be horseradish peroxidase or alkaline phosphatase.

In another embodiment, the solid support to which the antigen is bound is contacted with the sample under conditions such that any antibody present in the sample binds to the bound antigen and forms a complex therewith and is also contacted with a predetermined amount of antibody labeled with a detectable marker under conditions such that the labeled antibody competes with the antibody from the sample for binding to the antigen. In this method, the presence of antibody in the sample may be qualitatively determined or the amount of antibody in the sample may be quantitatively determined by determining the concentration of labeled antibody not bound to the solid support. The marker may be a radioisotope, fluorescent dye, or enzyme. Further, the antibody may be labeled with an enzyme and the labeled antibody not bound to the solid support removed and contacted with a substrate specific to the enzyme under conditions such that the enzyme reacts with the substrate to form a detectable product. In this embodiment, the enzyme is horseradish peroxidase or alkaline phosphatase.

In still another embodiment, the labeled antigen is in a solution which is contacted with the sample under conditions such that any antibody present in the sample binds to the labeled antigen and forms a complex therewith, which complex is immunoprecipitated. The presence of antibody in the sample is then qualitatively determined by detecting the labeled immunoprecipitate or the amount of antibody in the sample is quantitatively determined by measuring the amount of labeled immunoprecipitate.

The invention further provides a diagnostic method for determining the propensity of a subject toward mental illness. This method comprises obtaining a sample from the subject, contacting the sample with the antigen or the labeled antigen under conditions permitting antibodies to the neuronal antigen present in the sample to bind to the antigen, determining the amount of the antibodies bound to the antigen, and comparing the amount so determined with amounts obtained from subjects known to have mental illness or normal subjects and thereby diagnosing the subject's propensity toward or mental illness. The antigen may be labeled with a detectable marker.

The invention also provides a method for determining the propensity of a subject toward mental illness which comprises obtaining a sample from the subject, determining by any of the assays described above the amount of antibodies to the antigen present in the sample and comparing the amount so determined with amounts obtained from subjects known to have mental illness or normal subjects and thereby diagnosing the subject's propensity toward mental illness.

The invention further provides a diagnostic method for monitoring the progression or regression of the mental illness in a subject which comprises obtaining a sample from the subject, contacting the sample with the neuronal antigen or labeled neuronal antigen under conditions permitting antibodies to the antigen present in the sample to bind to the antigen, determining the amount of the antibodies bound to the antigen, and comparing the amount so determined with amounts previously obtained for the subject. The antigen may be labeled with a detectable marker.

The invention further provides a diagnostic method for monitoring the progression or regression of the mental illness in a subject which comprises obtaining a sample from the subject, determining by any of the assays described above the amount of antibodies to the antigen present in the sample and comparing the amount so determined with amounts previously obtained for the subject. In a preferred embodiment of the invention the mental illness being monitored is schizophrenia.

The invention further provides a method for treating a subject having mental illness which comprises contacting the subject's blood with the neuronal antigen under conditions such that the antigen binds to antibodies present in the subject's blood which are associated with mental illness and removing the antibodies bound to the antigen from the subject's blood. The antigen may be labeled with a detectable marker. The method may be effected by transfusing the subject's blood through a column in which the reagent is stationary and the blood flows past the reagent so that antibodies present in the blood are bound to the reagent and thereby removed from the blood.

In the preferred embodiments of the diagnostic and treatment methods of the subject invention, the mental illness is schizophrenia. However, all mental illnesses are encompassed by this invention.

This invention is illustrated in the Experimental Detail section which follow. These sections are set forth to aid in an understanding of the invention but are not intended to, and should not be construed to, limit in any way the invention as set forth in the claims which follow thereafter.

EXPERIMENTAL DETAILS

Autoantibodies have been implicated in the pathogenesis of schizophrenia, but to date, no specific antigens have been characterized (reviewed in DeLisi, L. E., Weber, R. J., Pert, C. B., Are there antibodies against brain in sera from schizophrenic patients. Biol Psychiatry 1985; 20: 94–119; Ganguli, Rabin B. S., Kelly R. H., Lyte M., Ragu U., Clinical and laboratory evidence of autoimmunity in acute schizophrenia. Annals New York Academy of Science 1987; 496: 676–685).

We have identified a protein antigen in human neuroblastoma cells that is recognized by autoantibodies from patients with schizophrenia. The protein migrates as a band with approximate mobility of 68 kD in SDS-polyacrylamide gels (SDS-PAGE), and $NH_2$-terminus amino acid sequencing of the purified band yielded the sequence alanine-lysine-(alanine)-valine-lysine-phenylalanine-glycine-alanine-aspartic acid-alanine-Xaa-alanine-leucine-methionine-leucine, SEQ ID NO: 2, (where ( ) means probable amino acid, and Xaa means unknown amino acid). Rabbit antibodies generated against a synthetic peptide containing the above sequence with alanine in position 3 and Xaa being lysine also reacted with the 68 kD band, providing an independent method for identifying the band.

METHODS AND MATERIALS

Patient Serum

Serum was obtained from patients with schizophrenia or with neurological disease. Serum was also obtained from normal subjects as controls.

Human Neuroblastoma Cells

The human neuroblastoma cell line, LAN-5, was grown in tissue culture flasks containing Dulbecco's modified medium with 15% fetal calf serum supplemented with 2 mM glutamine. 1 mM pyruvate, and 1% penicillin/streptomycin (Gibco, Grand Island, N.Y.) at 37° C. in 5% $CO_2$. (Mena, M. A. et al, Brain Res 1989, 486:286–96) They were harvested by gentle shaking, washed twice in PBS (0.2M NaCl, 0.05M $NaH_2PO_4$ pH 7.4) at 4° C. and stored at −20° C. until use.

Human Nueral Tissues

Normal human spinal cord and brain were obtained at autopsy within 12 hours after death from patients who died with non-neurological diseases. Myelin and non-myelin containing neuron and axon membrane preparations were obtained by sucrose density gradient centrifugation from spinal cord (Norton, W. T. Methods Enzymol. 1974, 32:435–44).

SDS-Polyacrylamide Gel Electrophoresis and Western Blot Analysis

Neuroblastoma cells and the central nervous system myelin and non-myelin fractions were dilapidated with acetone and the proteins solubilized by heating for 10 min at 65° C. in 2% dodecyl sulfate (SDS) containing the protease inhibitors 0.7 µM pepstatin, 1.1 µM leupeptin, 50 µg/ml trypsin inhibitor, 2 mM EDTA, 0.23 mM phenylmethylsulfonyl fluoride (PMSF) and 3 mM benzamidine (Sigma) (Hoffman, E. P., et al., Cell 1987, 51:919–28). The insoluble precipitates were then removed by centrifuging at 14,000 rpm for 15 min. at room temperature and the protein concentrations determined (Lowry, O. H., et al., J. Biol. Chem. 1951, 193:265–75). The proteins were then separated by SDS-PAGE using 7 or 12% polyacrylamide gels (Laemmli, U. K., Nature 1970, 227:680–85). One hundred µg of the protein was applied per lane. Following separation, the proteins were transferred electrophoretically onto nitrocellulose sheets (Towbin, H., et al., Proc. Natl. Acad. Sci. U.S.A. 1979, 76:4350–4354) and unreactive binding sites were saturated for 1 h at room temperature in a solution containing 8% BSA, 0.15M NaCl and 0.01M Trizma base, pH 7.4, and nitrocellulose strips were washed in washing solution containing 1% BSA, 0.05% Nonidet P-40 (NP 40), 0.15M NaCl and 0.01M Trizma base, pH 7.4. For investigations of human antibody binding, the blots were incubated with patient serum, diluted 1:100 in washing solution overnight at 4° C., and control strips were included with normal serum or with washing solution only. After washing, the strips were incubated for 2 h at 4° C. with biotinylated, affinity purified F(ab) fragments of antibodies to human IgA, IgG, or IgM, (Sigma) diluted 1:500 in washing solution. The strips were washed and incubated with avidin-biotin-peroxidase complexes (ABC method, Vector, Burlinghame, Calif.) for 1 h at room temperature. Reaction products were then developed in 0.025% hydrogen peroxide, 0.5% diaminobenzidine, 0.015M imidazole, 0.15M NaCl and 0.01M Trizma base, pH 7.4.

Isolation of the 68 kD Protein Band and $NH_2$-Amine Acid Sequencing

Neuroblastoma proteins were separated in parallel in multiple wells by SDS-PAGE, the gel stained with Coomassie blue, and the protein bands corresponding in mobility to the 68 kD band were cut out, pooled, eluted from the gel, dialyzed against water and lyophilized. The position of the 68 kD protein was determined in parallel lanes by Western blot using patient serum to identify the protein band. The isolated protein underwent a second cycle of purification by SDS-PAGE, then transferred onto polyvinylidine difluoride membrane where it was visualized with Coomassie blue, and sequenced using an Applied Biosystems gas-phase sequencer equipped with an on-line analyzer for Phenylthiohydantoin-derivitized amino acids, (Matsudaira P., Sequence from picogram quantities of proteins electroblotted onto polyvinylidene difluoride membranes. J. Biol Chem 1987, 262: 10035–10038; van den Berg L. H., Sadiq S. A., Thomas F. P., Latov N., Characterization of HNK-1 bearing glycoproteins in human peripheral nerve myelin. J. Neurosci Res 1990; 25, 295–299).

Generation of Antibodies to the Synthetic Peptide

A synthetic peptide with the sequence alanine-lysine-alanine-valine-lysine-phenylalanine-glycine-alanine-aspartic acid-alanine-lysine-alanine-leucine-methionine-leucine, SEQ ID NO: 1 was synthesized for purposes of immunization, the peptide was conjugated to keyhole limpet hemocyanin (KLH). A rabbit was then immunized with 1 mg of the conjugated peptide subcutaneously with complete Freund's adjuvant, and 6 weeks later, serum was removed by venopuncture and tested for the presence of antibodies that bound to the 68 kD protein antigen by Western blot. Pre-immune rabbit serum was tested in parallel as control.

RESULTS

Of 24 patients with schizophrenia tested, 7 had antibodies to a protein band with approximate mobility of 68 kD from human neuroblastoma cells by Western blot (FIG. 1). None of 19 control subjects tested, including 7 normal subjects and 12 with other diseases including neurological disease, had antibodies to the same protein band.

Figure 2:
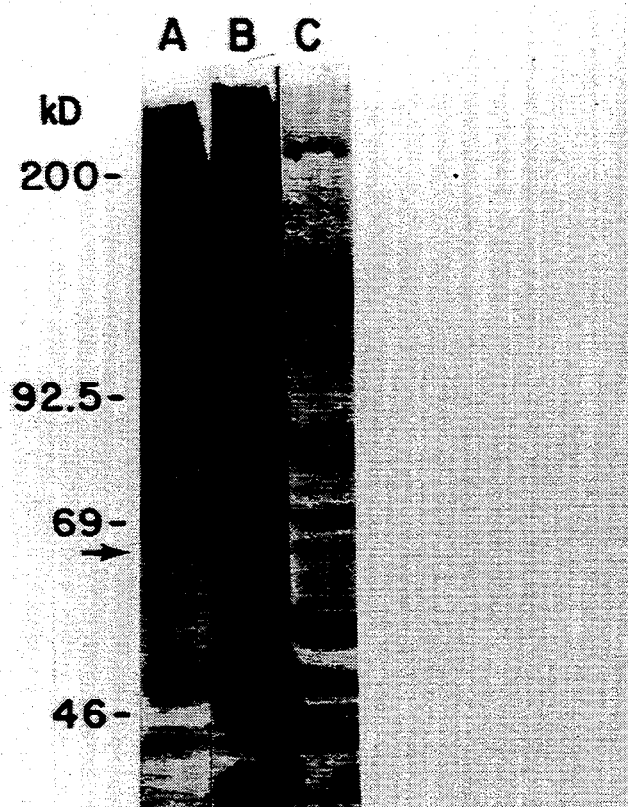
FIG. 2. Western blot analysis showing that the 68 kD protein is also present in human central nervous system tissue.

The 68 kD band was also present in the non-myelin membrane fraction of human central nervous system tissue (FIG. 2). However, the 68 kD band was more strongly immunostained in the extract from neuroblastoma cells, indicating that it was present there in greater concentrations.

Figure 3:
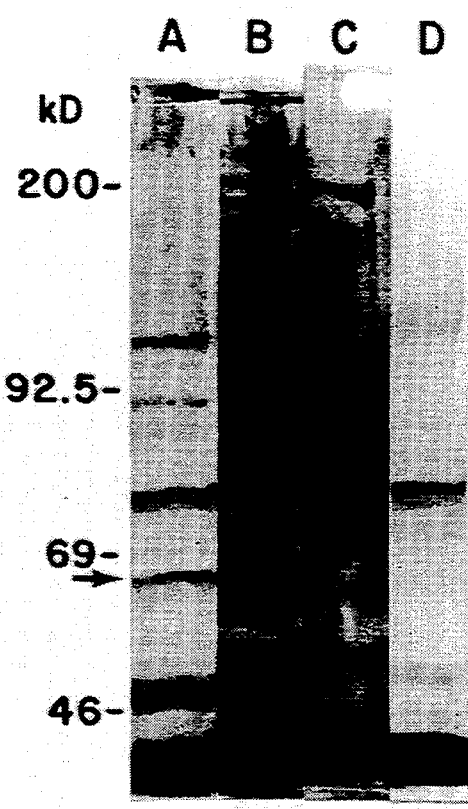
FIG. 3. Western blot analysis showing that the rabbit antibodies to a synthetic peptide react with the 68 kD protein band. Western blot analysis of neuroblastoma proteins, immunostained with A) serum IgG from a patient with schizophrenia; B) Serum IgG from a rabbit immunized with the synthetic peptide; C) Serum IgG from the same rabbit prior to immunization; and D) antibodies to rabbit IgG only. The serum IgG from the immunized rabbit but not from the pre-immune rabbit recognizes the same 68 kD protein band (arrow) that is seen by the serum IgG from the patient with schizophrenia.

$NH_2$-terminus amino acid sequence analysis of the isolated 68 kD band on Western blot yielded the sequence having an $NH_2$-terminus amino acid sequence as follows: alanine-lysine-(alanine)-valine-lysine-phenylalanine-glycine-alanine-aspartic acid-alanine-Xaa-alanine-leucine-methionine-leucine, SEQ ID NO: 1 (where () denotes the probable amino acid and Xaa denotes an unknown amino acid. Rabbit antibodies raised to a synthetic peptide encoding the sequence alanine-lysine-alanine-valine-lysine-phenylalanine-glycine-alanine-aspartic acid-alanine-lysine-alanine-leucine-methionine-leucine, SEQ ID NO: 1, reacted with the 68 kD band on Western blot (FIG. 3).

DISCUSSION

The cause of schizophrenia in most cases is unknown, but autoimmune mechanisms have been postulated to be responsible for the disease in some cases. Autoantibodies to brain constituents have been reported by several laboratories, but in most cases the results have not been reproducible, or the antigens were not well characterized (reviewed in DeLisi, L. E., Weber, R. J., Pert, C. B., Are there antibodies against brain in sera from schizophrenic patients. Biol Psychiatry 1985; 20: 94–119; Ganguli, Rabin B. S., Kelly R. H., Lyte M., Ragu U., Clinical and laboratory evidence of autoimmunity in acute schizophrenia. Annals New York Academy of Science 1987; 496: 676–685).

We found antibodies to a 68 kD protein of human neuroblastoma cells in approximately 30% of patients with schizophrenia but in none of the control subjects, suggesting that this autoantibody is specific for the disease. Sundin and Sten Thelander previously reported finding antibodies to several proteins in rat brain membranes including antibodies to proteins with approximate mobilities of 86 and 68 kD (Sundin U, Thelander S., Antibody reactivity to brain membrane proteins in serum from schizophrenia patients. Brain, Behavior, and Immunity 1989; 3, 345–358). However, approximately 50% of patients with schizophrenia and 3 of 50 normal subjects reacted with the protein bands, and no further characterization of the proteins was provided.

The peptide sequence obtained for the 68 kD protein band may belong to the antigen recognized by schizophrenic patients, or it may belong to a protein which co-migrates with the schizophrenia antigen in SDS-PAGE. The 68 kD band can be recognized by its reactivity with the rabbit antibodies raised to the corresponding peptide having the sequence alanine-lysine-alanine-valine-lysine-phenylalanine-glycine-alanine-aspartic acid-alanine-lysine-alanine-leucine-methionine-leucine, SEQ ID NO: 1.

What is claimed is:

1. A method for detecting in a sample from a subject the presence of an antibody to a purified antigen characterized as being reactive with an antibody associated with schizophrenia, located in neuronal cells, and having an $NH_2$-terminus amino acid sequence as follows: Ala-Lys-Xaa-Val-Lys-Phe-Gly-Ala-Asp-Ala-Xaa-Ala-Leu-Met-Leu (SEQ ID NO: 2); which method comprises treating the sample with the antigen under conditions permitting binding of the antibody to the antigen and detecting the presence of the antibody bound to the antigen and thereby detecting the presence of the antibody in the sample.

2. A method for detecting in a sample from a subject the presence of an antibody to a labeled antigen of claim 1 wherein the antigen is labeled with a detectable marker and the marker comprises an enzyme, a paramagnetic ion, biotin, a fluorophore, a chromophore, a heavy metal, or a radioisotope, which method comprises treating the sample with the labeled antigen of claim 1 under conditions permitting binding of the antibody of the antigen and detecting the presence of the antibody bound to the labeled antigen and thereby detecting the presence of the antibody in the sample.

3. The method of claim 1 or 2, wherein the sample comprises a biological fluid.

4. The method of claim 3, wherein the biological fluid is blood, plasma or serum.

5. The method of claim 2, wherein the detection of the presence of the antibody bound to the labeled antigen is effected spectrophotometrically.

6. The method of claim 2, wherein the labeled antigen is in a solution which is contacted with the sample under conditions such that any antibody present in the sample binds to the labeled antigen and forms a complex therewith, which complex is immunoprecipitated.

7. The method of claim 6, wherein the presence of antibody in the sample is qualitatively determined by detecting the labeled immunoprecipitate.

8. The method of claim 6, wherein the amount of antibody in the sample is quantitatively determined by measuring the amount of labeled immunoprecipitate.

9. A diagnostic method for aiding in determining the propensity of a subject toward schizophrenia which comprises obtaining a sample from the subject, determining by the method of claim 8 the amount of antibodies to the antigen present in the sample and comparing the amount so determined with amounts obtained from subjects known to have schizophrenia or normal subjects and thereby diagnosing the subject's propensity toward schizophrenia.

10. A diagnostic method for monitoring the progression or regression of schizophrenia in a subject which comprises obtaining a sample from the subject, determining by the method of claim 8 the amount of antibodies to the antigen present in the sample and comparing the amount so determined with amounts previously obtained for the subject and thereby monitor the progression or regression of schizophrenia in the subject.

11. A diagnostic method for aiding in determining the propensity of a subject toward schizophrenia which comprises obtaining a sample from the subject contacting the sample with the antigen of claim 2 under conditions permitting antibodies to the antigen of claim 2 present in the sample to bind to the antigen, determining the amount of the antibodies bound to the antigen, and comparing the amount so determined with amounts obtained from subjects known to have schizophrenia or normal subjects and thereby diagnosing the subject's propensity toward schizophrenia.

12. A diagnostic method for monitoring the progression or regression of schizophrenia in a subject which comprises obtaining a sample from the subject, contacting the sample with the antigen of claim 2 under conditions permitting antibodies to the antigen of claim 2 present in the sample to bind to the antigen, determining the amount of the antibodies bound to the antigen, and comparing the amount so determined with amounts previously obtained for the subject and thereby monitor the progression or regression of schizophrenia in the subject.

13. A diagnostic method for the aiding in determining the propensity of a subject toward schizophrenia which comprises obtaining a sample from the subject, contacting the sample with the antigen of claim 1 under conditions permitting antibodies to the antigen of claim 1 present in the sample to bind to the antigen, determining the amount of the antibodies to the antigen, and comparing the amount so determined with amounts obtained from subjects known to have schizophrenia or normal subjects and thereby diagnosing the subject's propensity toward schizophrenia.

14. A diagnostic method for monitoring the progression or regression of schizophrenia in a subject which comprises obtaining a sample from the subject, containing the sample with the antigen of claim 1 under conditions permitting antibodies to the antigen of claim 1 present in the sample to bind to the antigen, determining the amount of the antibodies bound to the antigen, and comparing the amount so determined with amounts previously obtained for the subject and thereby monitoring the progression or regression of schizophrenia in the subject.

15. The method of claim 2, wherein the antigen is immobilized on a solid support.

16. The method of claim 15 wherein the solid support is an ELISA plate.

17. The method of claim 15, wherein the solid support to which the antigen is bound is contacted with the sample under conditions such that any antibody present in the sample binds to the bound antigen and forms a complex therewith, removing any antibody which is not bound to the complex, contacting any complex so formed with a labeled antihuman antibody which specifically binds to any antibody present in the complex so as to form a second complex which includes the antigen, antibody, and labeled antihuman antibody.

18. The method of claim 17, wherein the antihuman antibody is labeled with a detectable marker.

19. The method of claim 18, wherein the detectable marker is a radioisotope, fluorescent dye, or enzyme.

20. A diagnostic method for aiding in determining the propensity of a subject toward schizophrenia which comprises obtaining a sample from the subject, determining by the method of claim 19 the amount of antibodies to the antigen present in the sample and comparing the amount so determined with amounts obtained from subject known to have schizophrenia or normal subjects and thereby diagnosing the subject's propensity toward schizophrenia.

21. A diagnostic method for monitoring the progression or regression of schizophrenia in a subject which comprises obtaining a sample from the subject, determining by the method of claim 19 the amount of antibodies to the antigen present in the sample and comparing the amount so determined with amounts previously obtained for the subject and thereby monitor the progression or regression of schizophrenia in the subject.

22. The method of claim 17, wherein the antihuman antibody is labeled with an enzyme and the second complex is contacted with a substrate specific to the enzyme under conditions such that the enzyme reacts with the substrate to form a detectable product.

23. The method of claim 22, wherein the enzyme is horseradish peroxidase or alkaline phosphatase.

24. The method of claim 17, wherein the presence of antibody in the sample is qualitatively determined.

25. The method of claim 17, wherein the amount of antibody in the sample is quantitatively determined.

26. The method of claim 15, wherein the solid support to which the antigen is bound is contacted with the sample under conditions such that any antibody present in the sample binds to the bound antigen and forms a complex therewith and is also contacted with a predetermined amount of antibody labeled with a detectable marker under conditions such that the labeled antibody competes with the antibody from the sample for binding to the antigen.

27. The method of claim 26, wherein the presence of antibody in the sample is qualitatively determined.

28. The method of claim 26, wherein the amount of antibody in the sample is quantitatively determined.

29. A diagnostic method for aiding in determining the propensity of a subject toward schizophrenia which comprises obtaining a sample from the subject, determining by the method of claim 28 the amount of antibodies to the antigen present in the sample and comparing the amount so determined with amounts obtained from subjects known to have schizophrenia or normal subjects and thereby diagnosing the subject's propensity toward schizophrenia.

30. A diagnostic method for monitoring the progression or regression of schizophrenia in a subject which comprises obtaining a sample from the subject, determining by the method of claim 28 the amount of antibodies to the antigen present in the sample and comparing the amount so determined with amounts previously obtained for the subject and thereby monitor the progression or regression of schizophrenia in the subject.

31. The method of claim 26, wherein the amount of antibody in the sample is quantitatively determined by determining the concentration of labeled antibody not bound to the solid support.

32. A diagnostic method for aiding in determining the propensity of a subject toward schizophrenia which comprises obtaining a sample from the subject, determining by the method of claim 31 the amount of antibodies to the antigen present in the sample and comparing the amount so determined with amounts obtained from subjects known to have schizophrenia or normal subjects and thereby diagnosing the subject's propensity toward schizophrenia.

33. A diagnostic method for monitoring the progression or regression of schizophrenia in a subject which comprises obtaining a sample from the subject, determining by the method of claim 31 the amount of antibodies to the antigen present in the sample and comparing the amount so determined with amounts previously obtained for the subject and thereby monitor the progression or regression of schizophrenia in the subject.

34. The method of claim 26, wherein the marker is a radioisotope, fluorescent dye, or enzyme.

35. The method of claim 26, wherein the antibody is labeled with an enzyme and the labeled antibody not bound to the solid support is removed and contacted with a substrate specific to the enzyme under conditions such that the enzyme reacts with the substrate to form a detectable product.

36. The method of claim 35, wherein the enzyme is horseradish peroxidase or alkaline phosphatase.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 15 amino acids
      ( B ) TYPE: amino acid
      ( C ) STRANDEDNESS: unknown
      ( D ) TOPOLOGY: unknown ( i i ) MOLECULE TYPE: peptide ( i i i ) HYPOTHETICAL: N ( i v ) ANTI-SENSE: N ( x i ) SEQUENCE DESCRIPTION: SEQ ID NO:1:

```
Ala  Lys  Ala  Val  Lys  Phe  Gly  Ala  Asp  Ala  Lys  Ala  Leu  Met  Leu
 1              5                        10                         15
```

( 2 ) INFORMATION FOR SEQ ID NO:2:

( i ) SEQUENCE CHARACTERISTICS:
      ( A ) LENGTH: 15 amino acids
      ( B ) TYPE: amino acid
      ( C ) STRANDEDNESS: unknown
      ( D ) TOPOLOGY: unknown ( i i ) MOLECULE TYPE: peptide ( i i i ) HYPOTHETICAL: N ( i v ) ANTI-SENSE: N ( x i ) SEQUENCE DESCRIPTION: SEQ ID NO:2:

```
Ala Lys Xaa Val Lys Phe Gly Ala Asp Ala Xaa Ala Leu Met Leu
 1           5                   10                  15
```